United States Patent [19]

Young et al.

[11] Patent Number: 4,954,638

[45] Date of Patent: Sep. 4, 1990

[54] LEUKOTRIENE BY AMIDES AND HYDRAZIDES

[75] Inventors: Robert N. Young, Senneville; Joshua Rokach, Chemedey, Laval, both of Canada; Edward C. Hayes, Lincroft, N.J.

[73] Assignees: Merck Frosst Canada, Inc., Kirkland, Canada; Merck & Co., Inc., Rahway, N.J.

[21] Appl. No.: 227,038

[22] Filed: Aug. 1, 1988

Related U.S. Application Data

[60] Division of Ser. No. 859,971, May 5, 1986, Pat. No. 4,767,745, which is a continuation of Ser. No. 665,596, Oct. 29, 1984, abandoned, which is a continuation-in-part of Ser. No. 565,263, Dec. 17, 1983, abandoned, which is a continuation-in-part of Ser. No. 370,229, Apr. 20, 1982, abandoned, and a continuation-in-part of Ser. No. 560,663, Dec. 12, 1983, abandoned.

[51] Int. Cl.$^5$ .................... C07D 207/404; C11C 3/00
[52] U.S. Cl. .................................. 548/546; 260/404.5; 260/404; 548/548
[58] Field of Search ................ 548/548, 546; 260/404, 260/404.5

[56] References Cited

U.S. PATENT DOCUMENTS 4,767,745  8/1988  Young et al. .................... 514/21

OTHER PUBLICATIONS

Prostaglandins, vol. 26, No. 4, (1983), pp. 605–613, Young et al.
Prostaglandins Leukotrienes and Medicine 13: 21–25, (1984).

Primary Examiner—Delbert R. Phillips
Assistant Examiner—Susan M. Perkins
Attorney, Agent, or Firm—Gabriel Lopez; Hesna J. Pfeiffer

[57] ABSTRACT

Leukotrienes may be conjugated with various proteins such as Bovine Serum Albumin (BSA) and Hemocyanin from Giant Keyhole Limpets (KLH) using 1,5-difluoro-2,4-dinitrobenzene or 6-N-maleimidohexanoic acid chloride as coupling agents.

These conjugates are useful as reagents in a newly developed immunoassay for leukotrienes, as well as having potential utility as chemical immunotherapeutic agents in the treatment of various allergic and chronic inflammatory diseases of the skin, lung, and airways, including asthma, allergic rhinitis, rheumatoid arthritis, and skin diseases such as psoriasis and eczema.

4 Claims, No Drawings

LEUKOTRIENE BY AMIDES AND HYDRAZIDES

This is a division of Ser. No. 06/859,971, filed May 5, 1986, now U.S. Pat. No. 4,767,745, which is a continuation of Ser. No. 06/665,596, filed Oct. 29, 1984, now abandoned, which is a continuation-in-part of Ser. No. 06/565,263, filed Dec. 17, 1983, now abandoned, which is a continuation-in-part of Ser. No. 06/730,229, filed Apr. 20, 1982 and a continuation-in-part of Ser. No. 06/560,663, filed Dec. 12, 1983, now abandoned.

RELATIONSHIP TO THE PRIOR ART

The concept of using conjugates of leukotrienes in a radioimmunoassay was described, by L. Levine, R. A. Morgan, R. A. Lewis, K. F. Austin, D. A. Clark, A. Marfat, and E. J. Corey, Proceeding of the National Academy of Sciences, U.S.A., Vol. 78, No. 12 7692 (1981) This method uses direct coupling through an activated acid derivative to the protein This method is much less effective than the present invention.

Bifunctional cross-linking reagents useful in preparation of protein-hapten conjugates have also been prepared, see Kitagawa, *J. Biochem.* 79, 233–236; and Kitagawa, *Chem. Pharm Bull* 29(4), 1130–1135; describing maleimido-succinimide derivatives. The present invention relates to conjugates of leukotrienes $C_4$, $B_4$, $D_4$ or $E_4$ (preferably $C_4$ and $B_4$) with a protein selected from hemocyanine from giant keyhole limpets (KLH), bovine serum albumin (BSA), human serum albumin, tetanus antigen, diphtheriae toxoid, or CRM 197 (a diphtheriae toxoid produced by a mutant of *Corynebacterium diphtheriae*), through the coupling agents 1,5-difluoro-2,4-dinitrobenzene or 6-N-maleimidoalkanoic acid chloride, preferably 6-N-maleimidohexanoic acid chloride, wherein the alkanoic moiety has 2 to 8 carbon atoms. The conjugates are useful in a sensitive and specific immunoassay and are also useful immunotherapeutic agents in the treatment of various allergic and chronic inflammatory diseases of the skin, lung and airways, including asthma, allergic rhinitis, rheumatoid arthritis, and skin diseases such as psoriasis and eczema. The present invention also relates to useful reagents for preparing such conjugates.

Leukotriene $C_4$ ($LTC_4$) has the following structure:

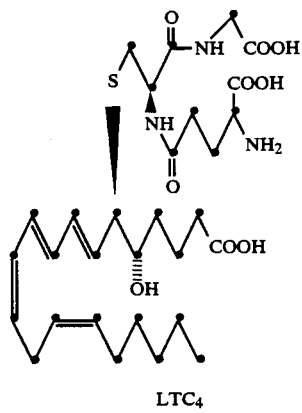

LTC₄

Leukotriene $B_4$ ($LTB_4$) has the following structure:

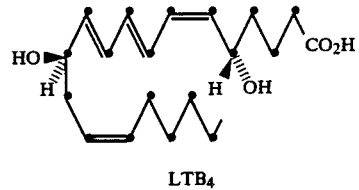

LTB₄

Leukotriene $D_4$ ($LTD_4$) has the following structure:

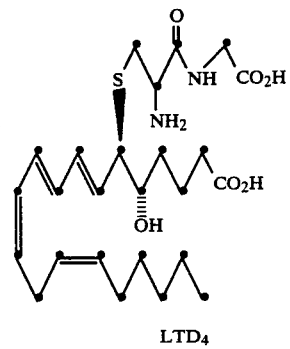

LTD₄

Leukotriene $E_4$ ($LTE_4$) has the following structure:

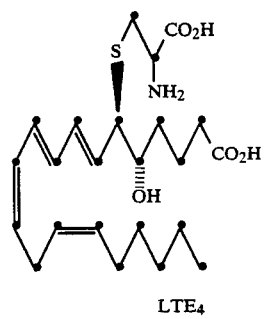

LTE₄

The present invention also relates to the following compounds which are useful in preparing the conjugates (especially the conjugates of $LTB_4$):

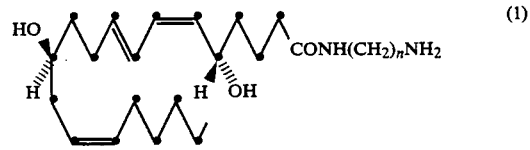

(1)

wherein n is 0 to 10, preferably 0 or 2 to 10, more preferably 0 or 3.

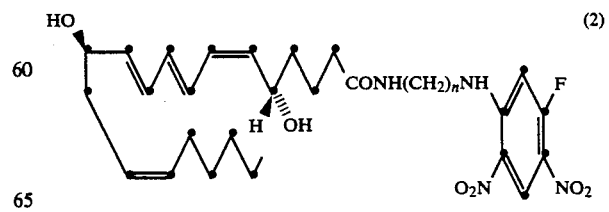

(2)

wherein n is 0 to 10, preferably 0 or 2 to 10, more preferably 0 or 3.

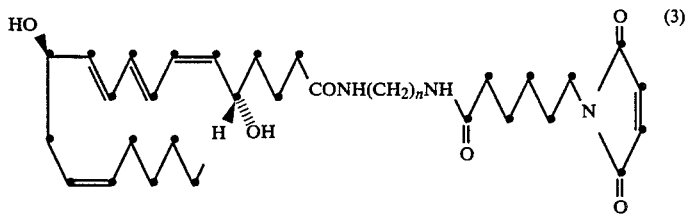

wherein n is 0 to 10, preferably 0 or 2 to 10, more preferably 0 or 3.

In the above three compounds, the compounds where n is 1 are likely to be less stable than the other compounds having the same generic formula.

The preparation of the conjugates of the present invention may be illustrated by reference to conjugates of $LTC_4$ and $LTB_4$.

For $LTC_4$, coupling procedures were selected so that the reactions took place on the free amino group of the glutamyl residue, thus retaining the most important parts of the $LTC_4$ molecule unchanged.

The general conjugation procedure utilized a stepwise method with well characterized intermediates. The strong UV absorption of the triene chromophore in $LTC_4$ ($\epsilon = 40,000$ at 280 nm) was used as a probe for determining coupling efficiencies and for monitoring the state of the $LTC_4$ molecules throughout the procedures.

Coupling ratios in the ranges of 5 to 15 equivalents of $LTC_4$ per 100,000 daltons of protein were desired.

Conjugates of $LTC_4$

Conjugations using 1,5-difluoro-2,4-dinitrobenzene as coupling agent:

The reagent, 1,5-difluoro-2,4-dinitrobenzene (DFDNB) reacts quite specifically with amino functions, allowing clean stepwise replacement of the two fluorine atoms (the second fluorine being replaced at a much slower rate). In addition, the strong and characteristic UV absorptions of the reagent, and its mono- and diamino substituted derivatives allows one to follow the course of the coupling procedure and to quantitate the final adducts by UV spectroscopy.

$LTC_4$ was found to react essentially quantitatively with excess DFDNB in pH 7.2 buffered aqueous methanol within 30 minutes The intermediates thus formed could be characterized by HPLC analysis, by the appearance of a strong UV band at 345 nm characteristic of 1-amino-5-fluoro-2,4dinitrobenzenes. After removal of methanol from the reaction the excess DFDNB could be removed by ether extraction. The intermediates could be further purified by HPLC but this was found to not offer any advantage and, in general, the crude reaction mixture was then allowed to react with protein in pH 8.5 buffer for two days in the dark. Final separation of the conjugates from unreacted $LTC_4$ or reagents was achieved by filtration on Sephadex G-50. The derived coupled products now showed UV absorptions at 342 and 420 nm characteristic of 1,5-diaminodinitrobenzenes as well as the characteristic absorptions of the triene system at 271, 282, and 291 nm in the case of the $LTC_4$ conjugates. In this manner, S-p-chlorophenacylglutathione when reacted in 10:1 molar ratio with BSA gave a conjugate with about 6 moles of hapten per mole of BSA.

Similarly, $LTC_4$ in 30 fold molar excess gave a conjugate with BSA with 9–10 moles $LTC_4$ per mole BSA, and $LTC_4$ in ca. 30 fold molar excess (calculated per 100,000 daltons protein), gave a conjugate with KLH with 11–12 equivalents $LTC_4$ per 100,000 daltons KLH.

Conjugation using 6-N-maleimidohexanoic acid chloride as coupling agent

Since this invention provides a second $LTC_4$ protein conjugate using a different spacer group, a number of potential coupling methods were examined A direct coupling using a reagent such as DCC or ECDI (6) was considered but quickly rejected due to the expectation that a heterogeneous mixture of adducts would be formed Also, preliminary experiments indicated that the efficiency of such a coupling would be low. The known agents, toluene diisocyanate and m-maleimidobenzoyl-N-hydroxysuccinimide ester were not used due to the possibility of immunological cross reactivity with respect to the spacer units between the two conjugates.

The coupling agent 6-N-maleimidohexanoic acid chloride provides rapid, selective functionalization of the glutamyl amino group of $LTC_4$, as well as high coupling efficiency.

The agent chosen was 6-N-maleimidohexanoic acid chloride which was readily prepared from 6-aminohexanoic acid. Other analogous reagents having from 2-8 carbon atoms in the chain can be used, e.g., 2-aminoacetic acid up to 8-amino octanoic acid.

The 6-N-maleimidohexanoic acid amide of $LTC_4$ was prepared by reacting a methanolic solution of $LTC_4$ tripotassium salt with the reagent (1.5 equivalents in dry THF) in the presence of excess $Et_3N$. HPLC analysis showed essentially complete conversion to the amide (eluting before $LTC_4$ on RP-HPLC) A portion of this adduct, isolated from HPLC, had UV characteristics essentially unchanged from those of $LTC_4$. For subsequent coupling with thiolated protein (KLH) the crude mixture (in pH 7.2 borate buffer) was used as such.

The thiolated protein used, in this case derived from KLH, was prepared by reaction with S-acetylmercaptosuccinic anhydride. As no report of thiolation of KLH could be found in the literature, trials were done to determine conditions for obtaining KLH with about 20 S-acetyl groups per 100,000 daltons protein [thio] content, after hydrolysis of the acetyl groups, was determined by Elleman's method. The S-acetylmercaptosuccinyl derivatized KLH was highly unstable to oxygen until further reacted with N-ethyl maleimide (NEM). However, once any free SH groups were thus reacted, the material could be handled and purified by Sephadex G-50 filtration.

Concentration of the resulting purified protein was accomplished by dialysis against a packing of anhydrous Sephadex G-200 resin. Just prior to coupling with derivatized $LTC_4$, the thiol groups were liberated by hydrolysis of the rigorously deoxygenated solution at pH 11.5 followed by reduction of the pH to 7.2.

This mixture was then reacted with the deoxygenated solution of the 6-N-maleimidohexanoic acid amide of $LTC_4$ in a ratio of 80 equivalents $LTC_4$ per 100,000 daltons KLH. After stabilization with NEM and purification by Sephedex G-50, the protein conjugate showed 7-10 moles LTC per 100,000 daltons KLH by UV analysis.

The protein solution has proven to be very stable during several months storage frozen at $-78°$ C.

More detailed examples follow. It is noted that IR spectra were recorded on a Perkin-Elmer 267 Grating Spectrophotometer. PMR spectra were recorded on a Varian EM-390 spectrometer. UV spectra were recorded on a Cary 210 spectrophotometer. Spectra were recorded in water unless otherwise indicated. Sephadex G-50 (medium grade) was obtained from Pharmacia Fine Chemicals.

Bovine Serum Albumin was obtained as crystallized and lyophilized grade from Sigma Chemical Co. and Hemocyanin (Keyhole Limpet) was obtained as lyophilized powder from Calbiochem Behring Corp. Leukotriene $C_4$ was synthetic material prepared in our laboratories using known procedures, Rokach et al., *Tet. Lett.*, 21, 1485 (1980).

Preparation of $LTB_4$ conjugates is illustrated by the following reaction schemes:

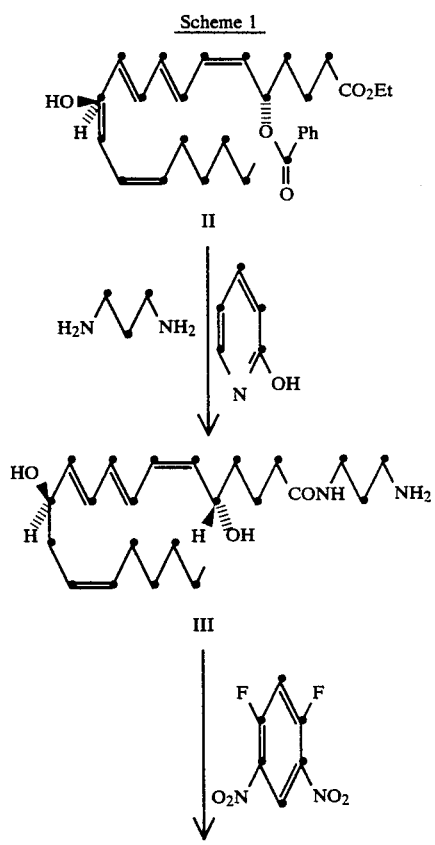

Scheme 1

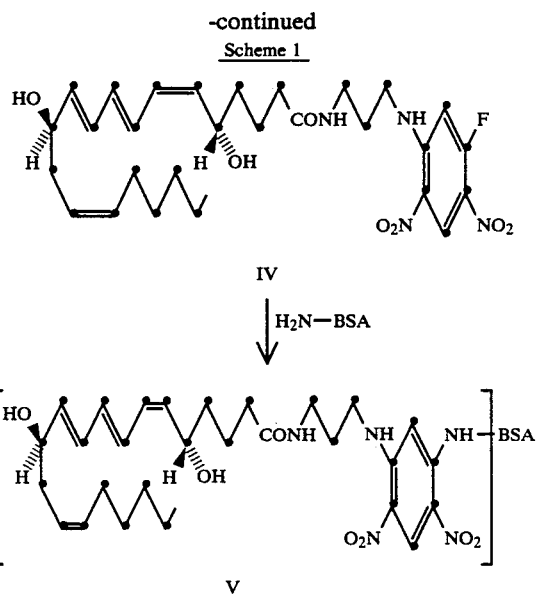

-continued
Scheme 1

This method makes use of the immediate synthetic precursor to LTB, Ethyl 5(S)benzoyloxy12(R)-hydroxy-6,14(Z)-8,10(E)-eicosatetraenoate (II). We reasoned that reaction of II with a volatile diamine such as 1,3-diaminopropane would at the same time remove the benzoate protecting group and convert the ethyl ester to the w-aminopropylamide, all under mild weakly basic conditions. The solvents could then be removed under vacuum leaving only a mixture of the product (III) and N-w-aminopropylbenzamide. In model studies, using ethyl 5-(4-octylphenyl)-5-benzoyloxypentanoate this reaction was found to be extremely sluggish, even in neat 1,3-diaminopropane. However, when a catalytic amount of 2-hydroxypyridine was added to the reaction mixture, the diester was smoothly converted to the desired aminoamide. When applied to the protected $LTB_4$ (II) a similar smooth conversion to III was effected. III could be reacted directly in the next step, after removal of the volatile components The aminoamide (III) was reacted with excess 1,5-difluoro2,4-dinitrobenzene in the presence of triethylamine to provide the adduct IV in high yield This product was purified by reverse phase HPLC and was fully characterized by UV and PMR spectroscopy Finally, IV reacted smoothly with bovine serum albumin (BSA) (mole ratio-12:1) in a mixture of dimethylformamide and pH 8.5 borate buffer to provide the conjugate V which was purified by chromatography on Sephadex G-50. UV spectral analysis indicated that the triene chromophore was unchanged and allowed the estimation that 5.5-8.3 moles of $LTB_4$ were coupled per mole of BSA. (45-70% coupling efficiency).

The aminoamide III could also be prepared by direct reaction of $LTB_4$-lactone with 1,3-diaminopropane at room temperature. This provided III in quantitative yield free of side products.

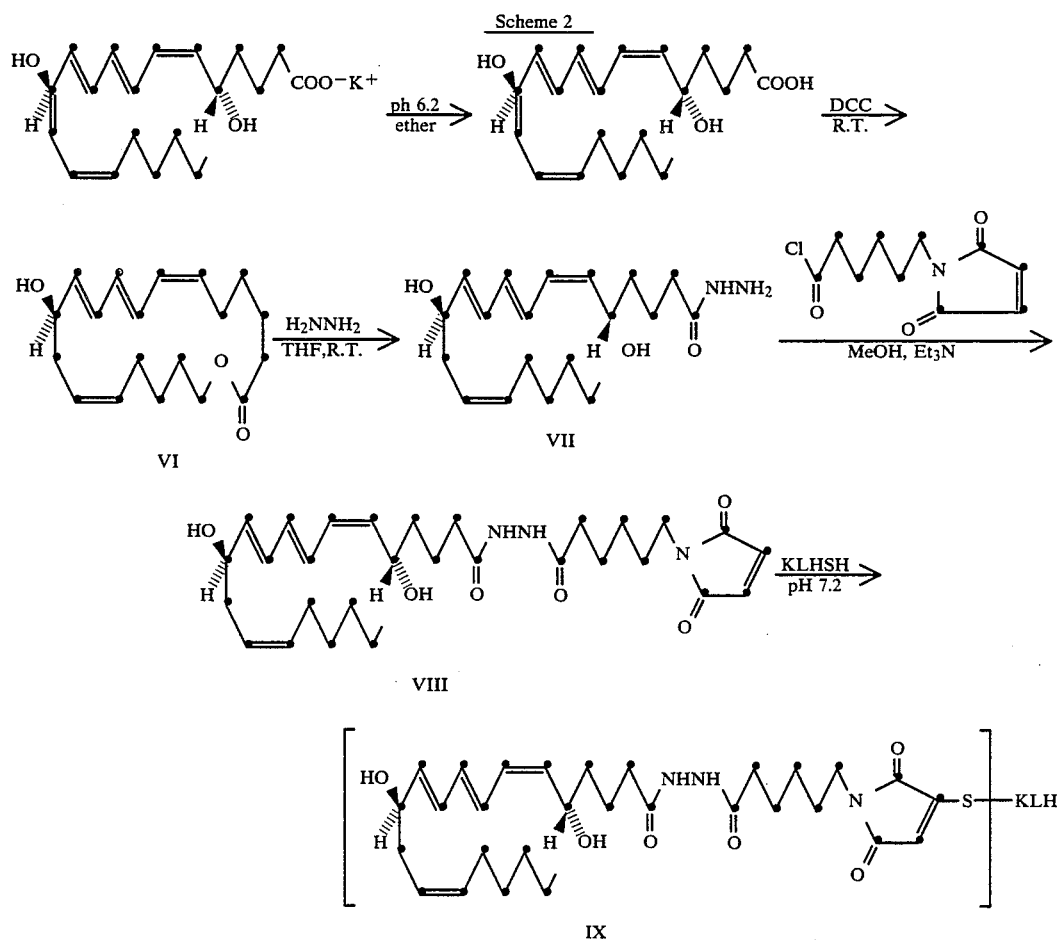

Scheme 2

Another type of LTB4 conjugate could be prepared as illustrated in Scheme 2. Lactone VI reacted cleanly with hydrazine to provide the hydrazide (VII) in quantitative yield. VII was reacted further with 6-N-maleimidohexanoic acid chloride to give the diacyl hydrazide (VIII) This material could be purified by reverse phase HPLC to remove the excess reagent by-products. However, attempts to concentrate the product in order to obtain a PMR spectrum led to partial decomposition apparently due to hydration or methanolysis of the maleimide system. It was found however, that the crude reaction product could be used in the subsequent coupling reaction VIII was reacted with thiolated KLH in a ratio of 50 moles of VIII per 100,000 daltons KLH, to provide the desired conjugate IX which was purified by filtration through Sephadex G-50. UV analysis indicated that 12 equivalents of LTB4 were bound per 100,000 daltons of KLH.

EXAMPLE 1

Conjugates of LTC4 Using 1,5-Difluoro-2,4dinitrobenzene as Coupling Agent

A. Conjugation of S-p-Chlorophenacylglutathione and Bovine Serum Albumin (BSA)

1,5-Difluoro-2,4-dinitrobenzene (120 mg, 0.59 mmol) in methanol (6 ml) was added to a solution of S-p-chlorophenacylglutathione (88 mg, 0.19 mmol) in 9 mL of phosphate buffer (pH 7.2, 0.1N). After stirring 12 hours at room temperature the methanol was removed in vacuo and the resulting aqueous solution was washed with ether. The aqueous layer was chromatographed on C-18 Silica Gel (eluting with methanol:water (1:1) to provide the pure adduct intermediate (105 mg). UV: $\lambda max$ ($\epsilon$) 260 (24,000), 347 nm (19,000). PMR (D$_{20}$): $\delta$8.62 (1H, d, J 32 7.5 Hz), 7.6 (2H, d, J=9Hz, A of AB), 7.1 (2H, d, J=9Hz, B of AB), 6.7 (1H, d, J=15Hz), 3.9 (2H, s, phenacyl CH$_2$).

The adduct (1.05 mg, $1.63 \times 10^{-6}$ mol) in water (0.1 mL) was added to a solution of BSA (10 mg, $1.49 \times 10-7$ mol) in borate buffer (pH 8.5, 0.2 N, 1 mL). After standing in the dark at room temperature for 71 hours the solution was centrifuged and filtered on Sephadex G-50 (1.5×75 cm) eluting with water. Fractions (10.5 mL) eluting after the void volume (55 mL) contained protein and were analyzed by UV. A sample of this solution diluted 5 times:had a UV spectrum (in H$_2$O ) $\lambda max$ (Absorbance) 342 (0.359), 425 nm (0.133). Assuming 8 mg of protein were recovered and assuming for the 1,5-diamino-2,4dinitrobenzene chromophor of ca. 27,000 (3) at 342 nm the UV indicated 6 moles of S-p-chlorophenacyllutathione were conjugated per mole of BSA.

B. Conjugation of Leukotriene C4 and Bovine Serum Albumin

Leukotriene C4 (tripotassium salt) (2.5 mg) was dissolved in 1 mL of phosphate buffer (pH 7.2, 0.1 N). 1,5-Difluoro-2,4-dinitrobenzene (1 mg) in methanol (0.6 mL) was added and the mixture was left 30 min. at room temperature The methanol was removed under a stream of $N_2$ and then in vacuo to remove final traces followed by extraction with ether (3×2 mL) to remove unreacted reagent. The last traces of ether were removed under $N_2$ and in vacuo. To this mixture was added bovine serum albumin (BSA) (10 mg) in borate buffer (0.2M, pH 8.5, 1 mL), and the mixture was left to stand at room temperature in the dark for two days. The reaction mixture was filtered on a column of Sephadex G-50 (1.5×75 cm) eluting with water and the yellow protein eluting in 18 mL, after the void volume, of ca. 55 mL, was collected. At about the 140 mL dead volume a peak considered to contain unreacted LTC eluted. Direct UV analysis on the protein fractions (combined) gave a spectrum λmax (A) 271 (sh), 282 (3.57), 291, 342 (1.835) and 420 nm (0.91). Assuming about 9 mg of protein were recovered, and assuming for the 1,5-diamino 2,4-dinitrobenzene of about 27,000 at 340 nm and for $LTC_4$ at 280 nm of 40,000, calculations based on the 282 nm absorption about 10.0 mole of $LTC_4$ per mole BSA while calculations based on the absorption of 342 nm indicated 9.1 moles $LTC_4$ per mole BSA.

C. Conjugation of Leukotriene $C_4$ and Hemocyanin from Giant Keyhole Limpets (KLH):

Leukotriene $C_4$ (tripotassium salt) (2.1 mg), and 1,5-difluoro-2,4-dinitrobenzene (8 mg) were reacted as in reaction A. To the resultant adduct was added KLH (15 mg) in borate buffer (pH 8.5, 0.2M, 0.83 mL) and the mixture was allowed to stand at room temperature 60 hours. At this time a precipitate of denatured KLH had formed which was removed by centrifugation (6 mg, dry weight). The supernatant was filtered on Sephadex G-50 as before yielding a yellow protein fraction eluting in 17 mL following the void volume which by UV analysis indicated 11-12 equivalents of $LTC_4$ per 100,000 daltons of KLH.

D. Conjugation of 2,4(E),6,9(7)-Pentadecatetraen-1-ol with BSA

A solution of DFDNB (2.04 g, 10 mmol) in dioxane (20 mL) was added to L-proline (0.58 g, 5 mmol) in phosphate buffer (pH 7.5, 0.1 N, 5 mL) and the mixture was stirred 2 hours at room temperature. The mixture was reduced to dryness and the residue was chromatographed on silica gel (eluting with chloroform:methanol (9:1) to yield N-2,4-dinitro5-fluorophenylproline as a foam (1.1 g).

PMR (CDCl$_3$): δ9.43 (1H, broad, exchanged by D$_{20}$, COOH), 8.55 (1H, d, $J_{H,F}$=7.5 Hz, H-3 of phenyl), 6.62 (1H, d, JH,F =15 Hz, H-6 of phenyl), 4.5 (1H, broad t, J=6Hz, proline methyne), 3.7-3.1 (2H, m), 2.7-1.9 ppm (4H, m).

To a mixture of 2,4(E),6,9(Z)-pentadecatetraen-1-ol (123 mg, 0.56 mmol) and the proline derivative above (170 mg, 0.57 mmol) in methylene chloride, at −10 C, were added successively, 1-cyclohexyl-3-(2-morpholinoethyl) carbodiimide methyl-p-toluenesulphonate (266 mg, 0.63 mmol) and pyrrolidinopyridine (9 mg, 0.06 mmol). The solution was stirred under $N_2$ at room temperature for 7 hours. The mixture was filtered and the filtrate was washed with water, 5% NaHCO$_3$, brine and dried over Na$_2$SO$_4$. The residue after concentration was chromatographed on silica gel [eluting with chloroform:ethano] (99.25:0.75)] to yield the pure adduct as an oil.

PMR (CDCl$_3$): δ8.57 (1H, d, J=7.5 Hz), 6.55 (1H, d, J=15 Hz), 6.7-5.2 (8H, m, olefinic), 4.65 (2H, d, J=6Hz, -COOCH$_2$-), 4.47 (1H, t, J=6Hz, proline methyne), 3.45 (2H, m), 2.95 (2H, m) 2.7-1.8 (6H, m), 1.5-1.2 (6H, m), 0.88 (3H, t). UV (dioxane: λmax (δ) 275 (48,700), 347nm (18,450). Anal. calcd for $C_{26}H_{32}N_3O_6F$:C, 62.26; H, 6.43; N, 8.38; F, 3.79. Found: C, 61.88; H, 6.72; N, 8.48; F, 3.47.

A suspension of the adduct (5 mg, 1×10$^{-5}$ mol and BSA (10 mg, 1.5×10$^{-7}$ mol) in dioxane (1 mL) and borate buffer (pH 8.5, 0.2M, 3 mL) was slowly stirred at room temperature for 4 days in the dark. The mixture was centrifuged and the suspernatant was filtered on Sephadex G-50 (1.5×75 cm), eluting with water. The protein fraction eluting in 7 ml after the void volume analyzed by UV for approximately 4 moles hapten per mole of BSA.

EXAMPLE 2

Conjugates of $LTC_4$ Using 6-N-Maleimidohexanoic Acid Chloride as Coupling Agent

A. Preparation of 6-N-Maleimidohexanoic Acid Chloride

6-Aminohexanoic acid (2 g, 0.02 mol) and maleic anhydride (2 g, 0.02 mol) were refluxed together in xylene (20 mL) under a Dean-Stark water separator such that the internal temperature reached ca. 165° C. The mixture was cooled, diluted with chloroform-methanol and washed with 1N hydrochloric acid. The organic layers were washed with water, dried, and reduced to dryness to yield a residue (1 g) which after chromatography on silica gel (eluting with 5% methanol-chloroform) provided pure 6-N-maleimidohexanoic acid, m.p. 84°-85° C. IR(KBr): 3300-2500 (COOH), 1700 cm$^{-1}$ (maleimide and COOH). PMR (CDC13): δ11.10 (1H, s, exchanged by D$_2$O, COOH), 6.72 (2H, s, maleimide CH), 3.53 (2H, t, J=7Hz), 2.34 (2H, t, J=7Hz), 1.6 ppm (6H, m). Mass spectrum: m/e 211 (M+). Anal. Calcd for $C_{10}H_{13}NO_4$: C, 56.87; H, 6.20; N, 6.63. Found: C, 56.87; H, 6.24; N, 6.62.

6-N-Maleimidohexanoic acid (50 mg 0.23 mmol) and α,α-dichloromethyl methyl ether (150 μl, 1.5 mmol) were refluxed together in anhydrous dichloromethane (1 mL) overnight. The mixture was reduced to dryness and the resultant highly hygroscopic solid (6-N-maleimidohexanoic acid chloride (54 mg) was used, freshly prepared, in the coupling reactions. IR (film): 1795 (COCl), 1700 cm$^{-1}$ (maleimide) PMR (CDCl$_3$): δ6.60 (2H, s, maleimide CH), 3.53 (2H, t, J=7Hz), 2.90 (2H, t, J=7Hz), 1.6 ppm (6H, m).

B. Reaction of 6-N-Maleimidohexanoic Acid Chloride with Leukotriene $C_4$ $LTC_4$ tripotassium salt (5 mg) was dissolved in anhydrous methanol (1 mL) and triethylamine (80 μL) under nitrogen and the acid chloride (25 μL of a solution of 10 mg acid chloride in 100 μL anhydrous THF) was added The reaction was stirred at room temperature and was followed by HPLC (Whatman Partisil M9 10/25 ODS, eluting with MeOH:H$_2$O:HOAc; 70:30:0.01, 4 mL/min) The adduct eluted at 4.8 min. and $LTC_4$ eluted at 6.6 min. After 10 and 30 min. about 15% of unreacted $LTC_4$ remained. More of the acid chloride solution (5 μL) was added and after a further 10 min. 5% unreacted $LTC_4$ remained. The reaction mixture was concentrated to 0.2 mL under a stream of $N_2$, diluted with borate buffer (pH 7 2, 0.1M, 0.5 mL) and the residual methanol was removed in vacuo. This solution had UV spectrum essentially unchanged from LTC$_4$ itself, and was used as such in reaction with thiolated KLH (see following).

C. Reaction of KLH with S-Acetylmercaptosuccinic Anhydride

KIH (60 mg) was dissolved in borate buffer (0.2M, pH 8, 1.5 mL) and centrifuged to remove denatured protein. The resultant solution analyzed for 24.6 mg/mL by UV [E$_{278}$ (mg/mL)=1.36]. The solution was deoxygenated (by three purges alternating high vacuum and pure N$_2$ flush) then treated under N$_2$ with S-acetylmercaptosuccinic anhydride (45 mg added in 5 mg portions over one hour). The pH was maintained at 8 by addition of 1N NaOH (total 400 $\mu$L). After standing one hour more, N-ethylmaleimide (20 mg in 0.1 mL MeOH) was added to bind any free thiol groups and stabilize the solution to air. After standing 1.5 hours more the solution was centrifuged and applied to a column Sephadex G-50 (1.5×75 cm) eluting with 0.1N saline buffered with 0.01N pH 6.2 phosphate buffer. Two fractions (7 mL) eluting after the void volume contained the bulk of the protein (2.4 mg/mL). An aliquot analyzed for thiol content, after hydrolysis at pH 11.5 for one hour, indicated 18 thiol groups per 100,000 daltons protein.

D. Coupling of 6-N-Maleimidohexanoic Acid Amide of LTC$_4$ and Thiolated KLH A solution of S-acetylmercaptosuccinate derivative of KLH (from reaction C) (10.8 mg, in 4.5 mL 0.1N saline, buffered to pH 6.2 with 0.01N phosphate) was rigorously deoxygenated and then the pH was raised to 11.5 with 1N NaOH (150 $\mu$L) under N$_2$ and the mixture was left at room temperature for one hour. The pH was then reduced to 7.2 by addition of deoxygenated 1N HCl (150 $\mu$L) and the solution of the 6-N-maleimidohexanoic acid amide derivative of LTC$_4$ from reaction B was added After standing 2 hours at room temperature, N-ethylmaleimide (1 mg in 10 $\mu$L methanol) was added and the mixture was left one hour more at room temperature This solution was applied to a Sephadex G-50 column (1.5×7.5 cm) eluting with 0.1N saline buffered to pH 6 with 0.01N phosphate. The protein fraction eluted with 85% in 11 mL after the void volume. Unreacted reagents eluted at the dead volume (150 mL). The protein solution was adjusted to pH 7.2 with 1N NaOH for storage.

Analysis of the protein solution by UV indicated 7–10 equivalents of LTC were coupled per 100,000 daltons protein The conjugates of LTC$_4$ with the proteins BSA and KLH have been used to raise antibodies with rabbits, at a dose of 200 $\mu$g/rabbit, approximately weighing 1 kg; the antibodies specifically recognize Leukotrienes C$_4$, D$_4$, and E$_4$. A detailed description of the antibody production, specificity, and the use of these conjugates in an immunoassay for the leukotrienes follows.

In addition to LTC$_4$ and the specific proteins used, it will be appreciated that other leukotrienes, such as LTD$_4$ and LTE$_4$ can be conjugated with other antigenic proteins such as tetanus antigen, human serum albumin (HSA), as well as diphtheriae toxide, tetanus antigen, and CRM 197 (from coryne bacterium diphtheriae) and other similar antigenic materials.

EXAMPLE 3

Immunization Using LTC$_4$ Conjugates

The following is the immunization regime used employing KLH-maleimido-LTC$_4$ as the immunogen.

Three 4 month old New Zealand White rabbits each received sub-cutaneous injections at multiple sites of 200 $\mu$g KLH-LTC in complete Freunds adjuvant followed in three weeks by sub-cutaneous injections at multiple sites with 100 $\mu$g LKH-LTC$_4$ in incomplete Freunds adjuvant. The rabbits were bled 10 days after the second injection and every three weeks thereafter. When a significant decline in the level of antibody was observed, the animals were boosted with 200 $\mu$g KLH-LTC$_4$ in incomplete Freunds adjuvant and the animals bled again on the same schedule.

The antigen BSA-DNP-LTC$_4$ was employed in a solid-phase-immuno-radioassay (SPIRA) in order to be used for the dectection of leukotrienes.

Polyvinyl chloride - 96 well microtiter plates (Dynatech Laboratories) were coated with antigen (BSA-DNP-LTC$_4$) by incubating 100 $\mu$l aliquotes of the antigen at 0.1 mg protein/ml in PBS for 18 h at 4° C. The wells were washed three times with 200 $\mu$l PBS and then unreacted sites in the wells were blocked by incubating a 200 $\mu$l aliqout of 10% horse serum in PBS in the wells for 2 h at 22° C. The wells were then washed three times with 200 $\mu$l of PBS-1.5 H.S.(1.5% horse serum in PBS). One hundred (100) $\mu$l of a reaction mixture containing a dilution of the immune or preimmune rabbit serum was added to the wells and the plates incubated for 4 h at 22° C. The 100 $\mu$l reaction employed for the titration of rabbit serum consisted of 50 $\mu$l of dilutions of the sera in PBS-1.5 H.S. and 50 $\mu$l of PBS-1.5 H.S. For competition analysis this reaction mixture consisted of 50 $\mu$l of a dilution of immune serum in PBS-1.5 H.S. which contained a limiting amount of leukotriene specific antibody and 50 $\mu$l of PBS-1.5. H.S. containing various concentrations of leukotrienes or chemically related compounds. This 100 $\mu$l reaction mixture was preincubated 1 h at 22° C. before it was added to the well of the microtiter plate.

The wells of the microtiter plate were then washed three times with 200 $\mu$l PBS-1.5 H.S. and then 100 $\mu$l of $^{125}$I-labeled rabbit anti-mouse $-[F^{(ab)}]_2$ fragments of rabbit anti-mouse IgG (H+L)]in PBS containing 10% horse serum was added to the wells and the plates incubated 4 h at 22° C. Approximately 2×10$^4$ cpm of the iodinated reagent was added to each well. After the incubation period, the wells were washed five times with 200 $\mu$l PBS-1.5 H.S. and once with 200 $\mu$l PBS. The wells were then cut from the plate and the radioactivity in each well was determined in a gamma counter.

The advantage of this assay is that, although the rabbits were immunized with KLH-maleimido-LTC$_4$, therefore antibodies are present in these animals against KLH, against the maleimido linker and against the hapten-LTC$_4$, however, antibodies directed against the KLH and the maleimido linker do not cross react or bind to the BSA or DNP linker of the material coated onto the the surface of the wells. Therefore the only antibodies that bind to the material coated on the wells (LTC$_4$-DNP-BSA) are directed against the LTC$_4$.

These rabbit LTC antibodies bind to the LTC$_4$ portion of the conjugate and they in turn are detected by adding a second species of antibody ($^{125}$I-labeled goat anti rabbit antibodies). There antibodies are radiolabeled with iodine and will bind to the rabbit antibodies which in turn are bound to $LTC_4$. The net result is, the more antibodies directed against $LTC_4$, the more radioactivity associated with the well.

In order to determine if free $LTC_4$ is in a biological sample, an aliquot is added to the plastic well. Some of this free $LTC_4$ will bind to the rabbit anti $LTC_4$ displacing if from the antigen coating which is bound to the surface. This results in a decrease in the number of counts ($^{125}I$) bound to the surface of the well and by comparing this decrease to the decrease in a standard curve where known amounts of free $LTC_4$ are added, the amount of $LTC_4$ in the sample can be determined.

The other compounds described in Examples 1 and 2 can be similarly used in an assay system, as reagents.

The antisera produced in rabbits by immunization with these conjugates can also be used in conjunction with radio-labelled leukotrienes $C_4$, $D_4$, or $E_4$ as the basis of a radioimmunoassay for Leukotrienes $C_4$, $D_4$, and $E_4$.

These conjugates are useful as chemical immunotherapeutic agents in the treatment various allergic and chronic inflammatory diseases of the skin, lung, and airways, including asthma, allergic rhinitis, rheumatoid arthritis, and skin diseases such as psoriasis and eczema.

$LTC_4$ ANTIBODY ASSAY

In a standard Guinea Pig Ileum assay, 4 tissues were set up in 10 ml baths of Kreb's buffer with atropine and pyrilamine both at $10^{-6}M$.

Standard contractions were observed using 10 µl of $2.7 \times 10^{-6}M$ LTC solution in a 10 ml bath, for a final concentration of $2.7 \times 10^{-9}M$ $LTC_4$.

The standard response tension was 1.1–2.0 grams.

20 µl of stock LTC solution was mixed with a varying amount (10 µl, 40 µl, 100 µl and 400 µl) of anti-LTC serum (rabbit)

(1 ml of serum contained $7.9 \times 10^{-9}M$ of specific anti-$LTC_4$ antibody).

The serum was incubated on ice (in the dark) for ½ hour before use.

Control samples were run using similar amounts of normal rabbit serum.

The mixed samples (15 µl, 30 µl, 60 µl and 210 µl respecitvely) were added to baths and the response recorded.

| RESULTS | |
|---|---|
| Volume of Antibody Serum | % of Control Response |
| 5 µl | 100.0 |
| 20 µl | 72.7 |
| 50 µl | 92.3 |
| 200 µl | 64.7 |
| Volume of Normal Serum | |
| 5 µl | 108.6 |
| 20 µl | 85.7 |
| 50 µl | 102.6 |
| 200 µl | 114.3 |

From the above results, clearly the anti-$LTC_4$ serum diminished the effect of $LTC_4$ in each sample. Thus the conjugates can be used to raise antibodies to $LTC_4$, $LTD_4$, $LTE_4$, in humans (in a manner similar to that employed herein in rabbits). The resulting circulating levels of antibodies would serve to diminish plasma levels of $LTC_4$, and $LTD_4$ and $LTE_4$ released during an asthmatic anaphylactic response and thus serve to alleviate the symptoms. Since the antibodies would be present during long periods of time, this would represent a long term asthma therapy.

EXAMPLE 4

Conjugates of $LTB_4$ Materials and Conditions

PMR spectra were recorded on a Varian EM-390 or Bruker WM-400 spectrometer. UV spectra were recorded on a Cary 210 spectrophotometer. Optical rotations were measured using a Perkin Elmer Model 241 Polarimeter Sephadex G-50 (medium grade) was obtained from Pharmacia Fine Chemicals.

Bovine serum albumin was obtained as crystallized and lyophilized grade from Sigma Chemical Co. and Hemocyanin (Keyhole Limpet) was obtained as lyophilized powder from Calbiochem Behring Corp.

1. Conjugation of $LTB_4$ with Bovine Serum Albumin

A.

5(S),12(R)-dihydroxy-6,14(Z)-8,10(E)-eicosatetraeonic acid δ-lactone ($LTB_4$-lactone) (VI):

5(S),12(R)-dihydroxy-6,14(Z)-8,10(E)-eico satetraenoate (12 mg) was stirred under nitrogen in methanol (1.5 mL) and water (0.4 mL) with postassium carbonate (22 mg) for 2.5 days at ambient temperature. Most of the methanol was removed under a stream of nitrogen (to leave about 0.4 mL volume) and the mixture was diluted with 0.1N pH 6.2 phosphate buffer (2.5 mL). The mixture was extracted with ether (5×2 mL) and the combined ether extracts were dried ($Na_2SO_4$) and reduced to dryness. UV analysis of the resulting oil indicated that 8 mg of $LTB_4$ free acid was thus obtained. The oil was dissolved in anhydrous ether (5 mL) and treated with dicyclohexylcarbodiimide (DCC) (20 mg) at 0° under nitrogen for 24 hours. TLC analysis (ethyl acetate: hexane 2:3) indicated about 50% conversion of LTB to the δ-lactone ($R_fLTB_4=0$, $R_f$ $LTB_4$ lactone=0.6). More DCC (30 mg) was added and after 2 days at 0° TLC indicated essentially complete conversion to the δ-lactone The mixture was concentrated to 1 mL under $N_2$, filtered, reduced to dryness, taken up in ethyl acetate:hexane (2:3) (1 mL) and chromatographed on silica gel column (10 g) eluting with the same solvent ot provide the δ-lactone contaminated with a small amount of dicyclohexylurea. This material was further purified by HPLC (Waters 10µ, µ-porasil; ethylacetate:hexane; (1:2); 4 mL/min) to provide the pure $LTb_4$ δ-lactone (VI) eluting at 5.7 min (6.3 mg, 77% yield from II). The lactone crystallized as fine needles from ether:hexane, mp 50.0–50.5° [α]RT/D = +231 0° (C=0.3, $CHCl_3$) UV: λmax (ε)(MeOH) 260 (37,200) 270 (50,000), 280 nm (39,400). δPMR (400 MHz) ($CDCl_3$): 0.87 (3H, t), 1.2–1.4 (6H, m), 1.65 (2H, m), 1.93 (2H, m), 2.03 (2H, q, CH , C-16), 2.32 (2H, m, CH, C-13), 2.48 (1H, dt, J=17.5, 7 Hz, one of $CH_2$, C-2), 2.62 (1H, dt, J=18, 5 Hz, one of CH2, C-2), 4.22 (1H, m, methine, C-12), 5.23 (1H, dt, J=10.5, 2Hz, methine, C-5), 5.35 (1H, dd), 5.45 (1H, t), 5.58 (1H, dd), 5.81 (1H, dd), 6.15 (1H, t), 6.29 (2H, m), 6.41 (1H, dd).

B.

N-(3-aminopropyl)-5-(S),12(R)-dihydroxy-6,14(Z)8,10(E)-eicosatetraenoic acid amide (III):

Method 1. $LTB_4$ δ-lactone (VI) 1.75 mg was dissolved in redistilled 1,3-diaminopropane (0.5 mL) and the mixture was left at room temperature for 18 hours. The excess diaminopropane was removed under high vacuum to give the amide III, quantitative yield,

[a]RT/D=−2° (C=0.17, CHCl$_3$). UV: λmax (ε) (MeOH) 259.5 (29,800) 269.5 (46,500), 280 (36,500). δPMR (400 MHz): 2.03 (2H, q, CH$_2$ C-16), 2.21 (2H, t, -CH$_2$-CONH-), 2.31 (2H, m, CH$_2$, C-13), 2.76 (2H, t, -CH$_2$—NH$_2$), 3.33 (2H, q, —CONH—CH$_2$—), 4.20 (1H, q, methine, C-12), 4.58 (1H, q, methine, C-5), 5.3–5.43 (2H, m), 5.55 (1H, dd), 5.78 (1H, dd), 6.05 (1H, t), 6.18–6.31 (2H, m), 6.36 (1H, broad NH, amide), 6.47 (1H, dd).

Method 2. Ethyl 5(S)-benzoyloxy-12(R)-hydroxy-6,14(Z)-8,10(E)-eicosatetraenoate (2.5 mg) and 2-hydroxypyridine (1.5 mg) were dissolved in 1,3-diaminopropane (0.5 mL) and the mixture was left at room temperature, under nitrogen, for 3 days. The excess diaminopropane was removed under high vacuum at room temperature to provide crude III which was used as such in the next reaction (UV: λmax 227, 260, 270, 280, 298 mm).

C. N-(3-[2,4-dinitro-5-fluorophenyl]aminopropyl)5(S), 12(R)-dihydroxy-6,14 (Z)-8,10(E)- eicosatetraenoic acid amide (IV):

The crude amino amide (III) from Step B, Method 2 (2 mg) in anhydrous methanol (400 μ) and triethylamine (8 μl) was treated with 1,5-difluoro2,4-dinitrobenzene (4 mg) in methanol 200 μl) at room temperature for 15 minutes at which time reverse phase TLC (RPTLC) (acetonitrile:water, 85:15:) indicated complete reaction of III (R$_f$=0.1) and the appearance of a new yellow product (R$_f$=0.7). The mixture was chromatographed on RPHPLC (Waters, 10 μ μbondapak, C-18, acetonitrile:water, 70:30, 1 mL/min) to provide the product IV (1.8 mg) [α]RT/D=18.9° (C=0.37, MeOH). UV λmax (MeOH) 260, 270, 280, 335, 380 (sh). PMR (400 MHz) (acetone-d$_6$: δ3.34 (2H, q, —CONH—CH$_2$—), 3.61 (2H, m, —CH$_2$—), 3.61 (2H, m, —CH$_2$-NH-Ar), 3.84 (2H, m, 2-OH), 4.14 (1H, m, methine, C-12) 4.58 (1H, m, methine, C-5), 5.42 (3H, m), 5.78 (1H, dd, J=14, 6Hz, H-11), 6.00 (1H, t, J=11Hz, H-7), 6.21 (1H, dd, J=14, 11Hz, H-10), 6.30 (1H, dd, J=14, 11Hz, H-9), 6.57 (1H, dd, J=14, 11Hz, H-8), 7.15 (1H, d, J$_H$F=15Hz), 7.27 (1H, broad, NH, amide), 9.00 (1H, d, J$_H$, F=8Hz), 9.15 (1H, broad, NH, amine).

D. Coupling of compound IV with Bovine Serum Albumin (BSA)

A solution of compound IV (from step C) (1.5 mg) in dimethylformamide (0.5 mL) was added to a solution of BSA (15 mg) in 0.2N pH 8.5 borate buffer (0.75 mL) and the mixture was allowed to stand in the dark under nitrogen and at room temperature for 4 days. The mixture was centrifuged and the clear supernatant was applied to a column of Sephadex G-50 (1.5×75 cm) eluting with water. The yellow protein fraction eluted cleanly in 20 mL, after the void volume of about 55 mL. At about the 140 mL dead volume a peak containing unreacted IV and byproducts eluted. UV analysis of the protein fractions gave a spectrum max 266, (sH), 273, 283, 336, 420 nn. Assuming 100% recovery of BSA from the column, calculations based on the peak at 273 nm, correcting for contributions due to BSA and to the dinitrobenzene chromophore, indicated that 5.5 moles of LTB$_4$ were coupled per mole of BSA. The absorption at 336 nm (assuming for the 1,5-diamino-2,4-dinitrobenzene chromophor of about 27,000) indicated that 8.3 moles of LTB$_4$ were coupled per mole BSA.

2. Conjugation of LTB4 with Hemocyanin from Keyhole Limpets (KLH)

LTB$_4$ δ-lactone (VI) (4 mg) was dissolved in a mixture of THF (1 mL) and 99% hydrazine hydrate (0.5 mL) and the mixture was stirred vigorously under nitrogen at room temperature for 0.5 hours. The mixture was extracted with ether (3×2 mL) and the combined organic layers were dried (Na$_2$SO$_4$) and evaporated to dryness under a stream of nitrogen and then in vacuo to provide the hydrazide VII (4.2 mg) [α]RT/D=8.9° (C=0.28, MeOH). UV λmax (ε)=260 (37,000) 269.5 (50,000), 280 (39,000) PMR (400 MHz) acetone-d$_6$) δ2.1 (2H, t), 2.27 (2H, m), 3.82 (1H, m, NH$_2$), 3.99 (1H, broad NH ), 4.14 (1H, m, methine, C-12), 4.56 (1H, m, methine, C-5), 5.3–5.5 (3H, m), 5.77 (1H, dd, J=14, 6Hz, H-11), 6.00 (1H, t, J=11Hz), 6.22 (1H, dd, J=14, 11Hz, H-10), 6.31 (1H, dd, J=14, 11Hz, H-9), 6.56 (1H, dd, J=14, 11 Hz, H-8), 8.22 (1H, broad, —CO—NH—).

B. Reaction of LTB hydrazide (VII) with 6-N-Maleimidohexanoic acid chloride

LTB$_4$ hydrazine (VII) 2.5 mg, 7×10$^{-6}$ moles), in anhydrous methanol (1 mL) and triethylamine (20 μL) was treated with a solution of 6-N-maleimidohexanoic acid chloride (8) (3 3 mg, 1.4×10$^{-5}$ moles) in anhydrous THF (100 μL) under nitrogen at room temperature. TLC analysis (chloroform:methanol, 85:15) indicated complete conversion to a less polar product. The mixture was reduced to dryness, and the residue was taken up in deoxygenated methanol (1.2 mL) and used as such in the next reaction. The product could be purified if desired by reverse phase HPLC (Waters 10μ, μ-Bondapak C-18; methanol:water; 75:25, 2mL/min), to give the pure adduct VIII eluting at 4.5 min UV δmax (MeOH) (δ): 260 (36,300), 270 (50,000), 280.5 nm (39,400).

On concentration to obtain PMR spectra some decomposition was noted by TLC. However the spectrum (400 MHz) (acetone d$_6$) contained a weak signal at 6.82 ppm indicating that the malemide unit was present although partially reacted.

C. Coupling of Compound VIII with Thiolated KLH:

S-Acetylmercaptosuccinylated KLH was prepared as previously described (8). The derivatized protein (KLHSAc) (10 mg) in 0.1N Saline buffered with 0.01 N pH 6.2 phosphate buffer (PBS) (5 mL) was rigorously deoxygenated; then the pH was raised to 11.5 by addition of 0.1N NaOH. After standing 1 hour nitrogen at room temperature, the pH was reduced to 7.2 by addition of 0.1N HCl. The adduct VIII in methanol (1.2 mL) from reaction B above, was added and the mixture was stirred slowly under nitrogen for 18 hours. N-ethylmalemide (5 mg) in methanol (0.1 mL) was added and the mixture was stirred 1 hour more. The methanol was removed under a stream of nitrogen during 1 hour, the mixture was centrifuged and the supernatant was filtered on Sephadex G-50 eluting with pH 6.2 PBS. The protein eluted with 95% in 19 ml after the void volume and gave a UV spectrum: λmax 264 (sH), 273.5, 283.5 nm. Assuming 9 mg of protein was recovered from the column and correcting the absorption at 273.5 nm for contributions due to coupled per 100,000 daltons KLH.

What is claimed is:

1. A compound of the formula:

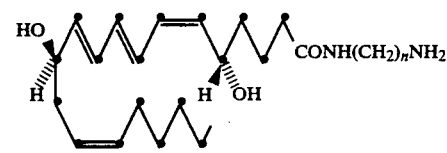

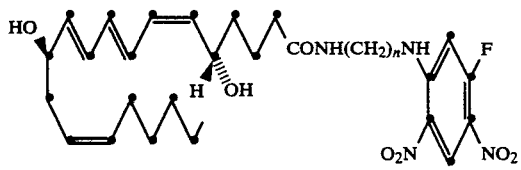

or

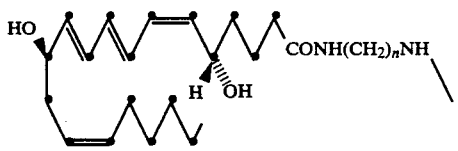

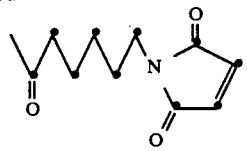

wherein n is 0 to 10.

2. A compound according to claim 1, wherein n is 0 or 2 to 10.

3. A compound according to claim 2, wherein n is 3.

4. A compound according to claim 1, said compound selected from:

5(S),12(R)-5,12-dihydroxy-6,14(Z),8,10,(E)eicosapenaeonic acid hydrazide;

5(S),12(R)-N'-(α-oxo-zeta-(2',5'-di-oxo-2',5'-dihydropyrrolo)hexane)-5,12-hydroxy-6,14(Z), 8,10(E)-eicosatetraenoic acid hydrazide;

N-(3-aminopropyl)-5-(S),12(R)-dihydroxy-6,14(Z)-8,10 (E)-eicosatetraenoic acid amide; and N-(3-[2,4-dinitro-5-fluorophenyl]aminopropyl)-5(S),12-(R)-dihydroxy-6,14(Z)-8,10(E)-eicosatetraenoic acid amide.

* * * * *

UNITED STATES PATENT AND TRADEMARK OFFICE
CERTIFICATE OF CORRECTION

PATENT NO. : 4,954,638

DATED : September 4, 1990

INVENTOR(S) : Young, et al.

It is certified that error appears in the above-identified patent and that said Letters Patent is hereby corrected as shown below:

On the title page, item [54] and in column 1, amend the title to read:

-- LEUKOTRIENE $B_4$ AMIDES AND HYDRAZIDES -- .

Signed and Sealed this

Seventh Day of January, 1992

Attest:

HARRY F. MANBECK, JR.

*Attesting Officer*      *Commissioner of Patents and Trademarks*